United States Patent [19]

Hromatka et al.

[11] 4,187,303

[45] Feb. 5, 1980

[54] THIAZINE DERIVATIVES

[75] Inventors: Otto Hromatka; Dieter Binder, both of Vienna, Austria; Paul Zeller, Allschwil; Rudolf Pfister, Basel, both of Switzerland

[73] Assignee: Hoffmann-La Roche Inc., Nutley, N.J.

[21] Appl. No.: 933,682

[22] Filed: Aug. 15, 1978

[30] Foreign Application Priority Data

Aug. 22, 1977 [LU] Luxembourg .............................. 78009

[51] Int. Cl.² ................... C07D 279/02; A61K 31/54
[52] U.S. Cl. ........................................ 424/246; 544/48
[58] Field of Search ........................... 424/246; 544/48

[56] References Cited

U.S. PATENT DOCUMENTS

| 3,591,584 | 7/1971 | Lombardino | 260/243 R |
|---|---|---|---|
| 3,646,021 | 2/1972 | Zinnes et al. | 260/243 R |
| 3,714,155 | 1/1973 | Zinnes et al. | 260/243 R |
| 3,808,205 | 4/1974 | Sircar et al. | 260/243 R |
| 3,821,211 | 6/1974 | Sircar et al. | 260/243 R |
| 3,822,258 | 7/1974 | Zinnes et al. | 260/243 R |
| 4,076,709 | 2/1978 | Hromatka et al. | 544/48 |
| 4,090,020 | 5/1978 | Binder et al. | 544/48 |
| 4,090,020 | 5/1978 | Binder et al. | 544/48 |

FOREIGN PATENT DOCUMENTS

| 2308305 | 9/1973 | Fed. Rep. of Germany . |
|---|---|---|
| 2534689 | 3/1976 | Fed. Rep. of Germany . |
| 2537070 | 3/1976 | Fed. Rep. of Germany . |
| 2016455 | 5/1970 | France . |
| 2282893 | 3/1976 | France . |
| 2341584 | 8/1977 | France . |
| 1308533 | 2/1973 | United Kingdom . |
| 1323283 | 7/1973 | United Kingdom . |

OTHER PUBLICATIONS

Lombardino et al., *J. Med. Chem.,* vol. 14, pp. 973–976 (1971).
Lombardino et al., *J. Med. Chem.,* vol. 14, pp. 1171–1175 (1971).
D. Pasquale et al., *Arch. Int. Pharmacodyn.,* vol. 203, pp. 92–100 (1973).
Lombardino et al., *J. Med. Chem.,* vol. 15, pp. 848–849 (1972).
Di Pasquale et al., *Agents and Actions,* vol. 5, pp. 256–263 (1975).
Wiseman et al., *Drug Research,* vol. 26, pp. 1300–1303 (1976).
Wiseman et al., *Pharmacologist,* vol. 18, p. 219 (1976).
Lombardino et al., *Drug Research,* vol. 25, 1629–1635 (1975).
Lombardino et al., *J. Med. Chem.,* vol. 16, pp. 493–496 (1973).
Wiseman et al., *Biochemical Pharmacology,* vol. 21, pp. 2323–2334 (1972).
Rau et al., *Excerpta Med. Found.,* Int. Cong. Ser. No. 299, p. 117, Abst. 396 (1973).
Zinnes et al., *J. Med. Chem.,* vol. 16, pp. 44–48 (1973).

*Primary Examiner*—John M. Ford
*Attorney, Agent, or Firm*—Jon S. Saxe; George M. Gould; Peter R. Shearer

[57] ABSTRACT

Thienothiazine derivatives of the formula

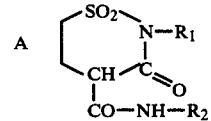

wherein A, $R_1$ and $R_2$ are as hereinafter set forth, and their tautomers are described. The thienothiazine derivatives are useful as anti-inflammatory, analgesic, anti-rheumatic and antithrombotic agents.

12 Claims, No Drawings

THIAZINE DERIVATIVES

BRIEF SUMMARY OF THE INVENTION

The thienothiazine derivatives of the present invention are characterized by the formula

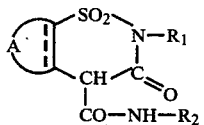    I wherein A together with the two carbon atoms forms the grouping

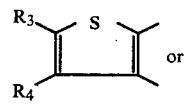    (a)

or

    (b)

and the broken line indicates the double bond which is present in grouping (a), $R_1$ is lower alkyl, $R_2$ is the residue of an aromatic heterocycle of 1 to 4 hetero atoms, which may be optionally substituted by one or two lower alkyl groups, or a phenyl or benzyl group optionally substituted by halogen, hydroxy, lower alkyl, trifluoromethyl or lower alkoxy, and $R_3$ and $R_4$, independently, are hydrogen or lower alkyl, salts thereof with pharmaceutically acceptable bases and, when $R_2$ is the residue of a basic heterocycle, salts thereof with pharmaceutically acceptable acids.

In another aspect, the invention relates to pharmaceutical preparations containing a compound of formula I above.

DETAILED DESCRIPTION OF THE INVENTION

The thienothiazine derivatives of the invention are compounds characterized by formula I, hereinbefore, or alternatively characterized by the formulas

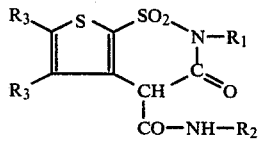    I' and

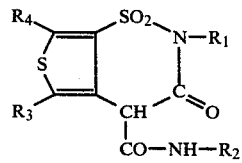    I'' wherein $R_1$ is lower alkyl, $R_2$ is the residue of an aromatic heterocycle containing 1 to 4 hetero atoms which may be optionally substituted by one or two lower alkyl groups, or a phenyl or benzyl group optionally substituted by halogen, hydroxy, lower alkyl, trifluoromethyl or lower alkoxy, and $R_3$ and $R_4$, individually, are hydrogen or lower alkyl, salts thereof with pharmaceutically acceptable bases and, when $R_2$ is the residue of a basic heterocycle, salts thereof with pharmaceutically acceptable acids.

The compounds of formula I can also exist in the tautomeric form characterized by the formula

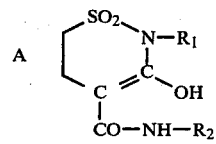    Ia wherein A, $R_1$ and $R_2$ are as previously described.

The compounds of formulas I' and I'', which are encompassed by formula I, in their tautomeric forms are characterized, respectively, by the formulas

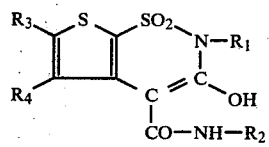    I'a and

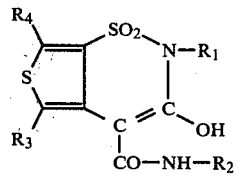    I''a wherein $R_1$, $R_2$, $R_3$ and $R_4$ are as previously described.

As used herein, the term "lower alkyl" denotes a straight-chain or branched-chain saturated hydrocarbon group containing 1 to 4 carbon atoms, for example, methyl, ethyl, propyl, isopropyl, tert.butyl or the like. The term "lower alkoxy" denotes hydrocarbonoxy groups containing 1 to 4 carbon atoms. The term "halogen" denotes chlorine bromine, fluorine and iodine. The term "residue of an aromatic heterocycle containing 1 to 4 carbon atoms and optionally substituted by one or two lower alkyl groups" comprises residues of 5-membered or 6-membered aromatic heterocycles containing 1 to 4 nitrogen and/or oxygen and/or sulfur atoms and optionally substituted by one or two lower alkyl groups, such as 2-thiazolyl, 4-methyl-2-thiazolyl, 4,5-dimethyl-2-thiazolyl, 5-methyl-1,3,4-thiadiazolyl, 2-pyrazinyl, 2-pyrimidinyl, 1,2,4-triazin-3-yl, 2-pyridyl, 3-pyridyl, 4-pyridyl, 3-methyl-2-pyridyl, 4-methyl-2-pyridyl, 5-methyl-2-pyridyl, 6-methyl-2-pyridyl, 4,6-dimethyl-2-pyridyl, 5-isoxazolyl, 5-methyl-3-isoxazyl, 3,4-dimethyl-5-isoxazyl, 2,6-dimethyl-4-pyrimidinyl, 6-methyl-2-pyridyl, 1,2,3,4-tetrazol-5-yl and the like.

In a preferred class of thienothiazine derivatives of the invention, $R_3$ and $R_4$ are hydrogen. $R_1$ preferably is methyl. $R_2$ preferably is phenyl or halogenated phenyl.

In accordance with the process of the invention, the thienothiazine derivatives, that is, the compounds of formula I, salts thereof with pharmaceutically acceptable bases and, when $R_2$ is the residue of a basic heterocycle, salts thereof with pharmaceutically acceptable acids, can be prepared by reacting a compound of the formula

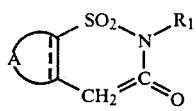   II wherein A and $R_1$ are as previously described,
in the presence of a strong base with an isocyanate of the formula $O=C=N-R_2$   III wherein $R_2$ is as previously described,
and, if desired, converting an obtained compound of formula I into a salt with a pharmaceutically acceptable base or, when $R_2$ is the residue of a basic heterocycle, into a salt with a pharmaceutically acceptable acid.

In accordance with the process of the invention, a compound of formula II is reacted with an isocyanate of formula III in the presence of a strong base. Suitable strong bases comprise alkali amides, alkali metal hydrides, alkaline earth metal hydrides, alkali metals and alkaline earth metals. The reaction is preferably carried out under an atmosphere of an inert gas, for example, nitrogen, at a temperature in the range of from about 0° C. to about 50° C., preferably at room temperature, and in the presence of an inert polar solvent, for example, toluene, dioxane, dimethylformamide, dimethylsulfoxide or hexamethylphosphoric acid triamide (HMTP).

The isocyanate starting materials of formula III are known compounds or can be prepared in an analogous manner to the known compounds.

The starting materials of formula II can be prepared as illustrated in the following Formula Schemes wherein $R_1$ is as previously described.

Formula Scheme I

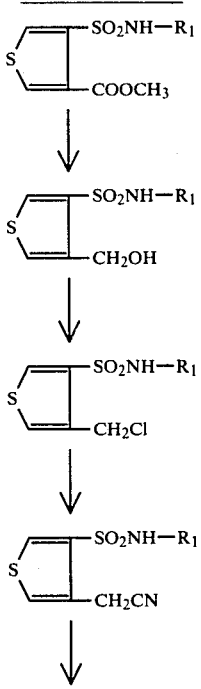

-continued
Formula Scheme I

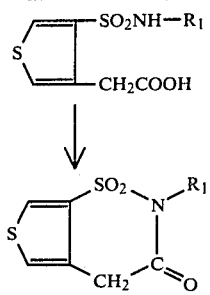

Formula Scheme II

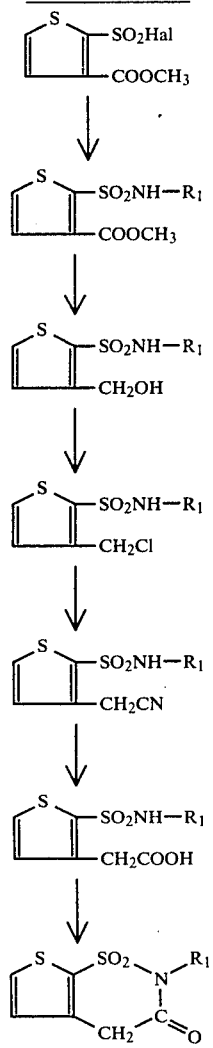

The compounds of formula I are acidic and can form pharmaceutically acceptable salts with pharmaceutically acceptable bases. Suitable pharmaceutically acceptable bases are, for example, alkali metals such as lithium, sodium and potassium, alkaline earth metals such as magnesium and calcium, and amines such as triethanolamine, diethylaminoethanol, triethylamine, trimethylamine, diethylamine, and the like. Compounds of formula I which contain a basic heterocycle $R_2$ can also form pharmaceutically acceptable acid addition salts with pharmaceutically acceptable strong acids. Such strong acids comprise, in particular, mineral acids, for example, hydrochloric acid.

The thienothiazine derivatives provided by the present invention possess antiinflammatory, analgesic, antirheumatic and antithrombotic acitivity. These valuable pharmacological properties can be determined or demonstrated utilizing standard methods; for example, the known kaolin-paw edema test on the rat. In this test, an acute local inflammation is produced in the right hind paw of the rat by intradermal injection of 0.1 ml. of a 10% kaolin suspension (bolus alba). The substance to be tested is administered orally. The following parameters are measured:

1. Diameter of the paw in mm, as an expression of the intensity of inflammation;
2. Pressure in g. on the paw to determine the pain threshold.

The substance to be tested is administered 0.5 hour before and 3.5 hours after the kaolin injection and the aforementioned parameters are measured 4 hours after the kaolin injection. The edema-inhibiting effect is given in percentages based on the difference in the edema-intensity between untreated animals and animals treated with the substance to be tested and the antinosiceptive activity is given by the percentage increase in the pain threshold.

In the foregoing test, compounds of formula I have shown an edema inhibition and an increase in the pain threshold. Thus, for example, the compound 3-hydroxy-2-methyl-4-(bromophenylcarbamoyl)-2H-thieno[3,2-e]-1,2-thiazine 1,1-dioxide applied orally at a dose of 10 mg/kg shows a 25% inhibition of the edema and a 51% increase of the pain threshold. In addition, as can be demonstrated in an appropriate standard test, they inhibit blood platelet aggregation and, accordingly, also have antithrombotic properties.

The compounds of formula I have an activity qualitatively similar to that of phenylbutazone which is known for its therapeutic use and properties.

The thienothiazine derivatives of formula I of the invention and their salts can be used as medicaments. For example, they can be used in the form of pharmaceutical preparations which contain them in association with a compatible pharmaceutical carrier material. Such carrier material can be an organic or inorganic inert carrier material suitable for enteral or parenteral administration, for example, water, gelatin, gum arabic, lactose, starch, magnesium stearate, talc, vegetable oils, polyalkyleneglycols, petroleum jelly, or the like. The foregoing pharmaceutical preparations can be made up in solid form, for example, as tablets, dragees, suppositories or capsules, in semi-solid form, for example, as salves, or in liquid form, for example, as solutions, suspensions or emulsions. The pharmaceutical preparations may be sterilized and/or may contain adjuvants such as preserving, stabilizing or emulsifying agents, salts for varying the osmotic pressure or buffers. They can also contain still other therapeutically valuable substances.

The Examples which follow further illustrate the invention. All temperatures are in degrees Centigrade, unless otherwise stated. The end-products are described as the enol tautomers (see formulae I', I'a and I"a).

EXAMPLE 1

1.8 g (8.3 mmol) of 3,4-dihydro-2-methyl-3-oxo-2H-thieno[3,2-e]-1,2-thiazine 1,1-dioxide are stirred for 24 hours at room temperature under nitrogen with 1.6 g (8.3 mmol) of p-bromophenylisocyanate and 0.84 g (8.3 mmol) of triethylamine in 20 ml of absolute dimethyl sulfoxide. Thereafter, the mixture is poured into 50 ml of 2-N hydrochloric acid and 20 g of ice. The separated precipitate is filtered off under suction and washed neutral with water. The filter residue is taken up in 200 ml of methylene chloride, dried over sodium sulfate, stirred with 1 g of active carbon and filtered. The filtrate is extracted with four 100 ml portions of semi-saturated sodium carbonate solution, each of the organic phases being re-extracted with a small amount of methylene chloride. The combined aqueous phases are acidified to pH 1 with concentrated hydrochloric acid. The separated product is extracted with three 100 ml portions of methylene chloride. The combined organic phases are dried over sodium sulfate and evaporated, whereby the product crystallizes out. For purification, the product is recrystallized from ca 30 ml of methanol to give 3-hydroxy-2-methyl-4-(4-bromophenylcarbamoyl)-2H-thieno[3,2-e]-1,2-thiazine 1,1-dioxide of melting point 197°-199° C.

The starting material can be prepared as follows:

12 g (50 mmol) of 2-chlorosulfonylthiophene-3-carboxylic acid methyl ester are dissolved in 120 ml of absolute chloroform. Thereupon, dry methylamine is conducted into the solution at room temperature until a moist pH paper shows an alkaline reaction with the solution. Thereafter, the mixture is stirred for a further 3 hours at room temperature, whereby a moist pH paper must give an alkaline reaction with the solution to the end. The mixture is poured into 100 ml of 2-N hydrochloric acid. The organic phase is separated and the aqueous phase is extracted with two 50 ml portions of chloroform. The combined organic phases are dried over sodium sulfate and evaporated to give an oil which crystallizes out upon cooling. There is obtained 2-N methylsulfamoylthiophene-3-carboxylic acid methyl ester of melting point 106°-107° C.

10.6 g (45 mmol) of 2-N-methylsulfamoylthiophene-3-carboxylic acid methyl ester and 10.2 g (0.27 mol) of sodium borohydride are suspended in 300 ml of absolute ether and the suspension is heated to boiling. 26 g (0.81 mol) of absolute methanol, diluted with 50 ml of absolute ether, are added dropwise to the boiling suspension over a period of 30 minutes and then the mixture is boiled under reflux for 1 hour. After cooling, the mixture is cautiously hydrolyzed with 70 ml of half-concentrated hydrochloric acid and the separated precipitate is filtered off under suction. The phases of the filtrate are separated. The aqueous phase is extracted with three 200 ml portions of ether. The filter residue is digested with three 200 ml portions of ether. The combined organic phases are dried over sodium sulfate and evaporated to give a non-crystallizing oil. There is obtained 3-hydroxymethyl-2-N-methylthiophenesulfonamide.

7.5 g (36.1 mmol) of 3-hydroxymethyl-2-N-methylthiophenesulfonamide are boiled under reflux with 50 ml of thionyl chloride for 15 minutes. Thereafter, the mixture is evaporated to dryness in a water-jet vacuum. The residue is taken up in 150 ml of methylene chloride and stirred with saturated sodium bicarbonate solution until the aqueous phase has an alkaline reaction. The phases are separated. The aqueous phase is extracted with two 50 ml portions of methylene chloride. The combined organic phases are dried over sodium sulfate and evaporated to give an oil which crystallizes out in the cold. There is obtained 3-chloromethyl-2-N-methylthiophenesulfonamide of melting point 52°-53° C.

7.9 g (32.7 mmol) of 3-chloromethyl-2-N-methylthiophenesulfonamide and 4.7 g (72 mmol) of potassium cyanide are heated to 80° C. for 15 minutes in 40 ml of triethyleneglycol. Thereafter, the mixture is poured into 100 ml of 2-N hydrochloric acid and 50 g of ice and extracted with three 200 ml portions of methylene chloride. The combined organic phases are dried over sodium sulfate, stirred with 1 g of active carbon, filtered and evaporated to give a noncrystallizing oil. There is obtained 3-cyanomethyl-2-N-methylthiophenesulfonamide.

6.9 g (29.5 mmol) of 3-cyanomethyl-2-N-methylthiophenesulfonamide are boiled under reflux for 2 hours with 2.6 g (64.8 mmol) of sodium hydroxide in 70 ml of water. Thereafter, the mixture is acidified to pH 3 with ca 6 ml of concentrated hydrochloric acid, neutralized to pH 8 with solid sodium bicarbonate and extracted with two 100 ml portions of methylene chloride. The organic phases are discarded. The aqueous phase is acidified to pH 1 with concentrated hydrochloric acid and extracted for 24 hours with methylene chloride. The organic phase is dried over sodium sulfate and evaporated, the product crystallizing out. There is obtained 3-(2-N-methylsulfamoyl)-thiopheneacetic acid of melting point 134°–135° C. 5.2 g (22 mmol) of 3-(2-N-methylsulfamoyl)-thiopheneacetic acid are boiled under reflux for 15 minutes with 50 ml of thionyl chloride. Thereafter, the mixture is evaporated to dryness in a water-jet vacuum. The residue is taken up in 100 ml of methylene chloride and stirred with saturated sodium bicarbonate solution until the aqueous phase has an alkaline reaction. The phases are separated. The aqueous phase is extracted with two 50 ml portions of methylene chloride. The combined organic phases are dried over sodium sulfate and evaporated, the product crystallizing out. For purification, the product is digested with a small amount of ice-cold methanol. There is obtained 3,4-dihydro-2-methyl-3-oxo-2H-thieno[3,2-e]-1,2-thiazine 1,1-dioxide of melting point 136°–137° C.

EXAMPLE 2

1 g (4.6 mmol) of 3,4-dihydro-2-methyl-3-oxo-2H-thieno[3,2-e]-1,2-thiazine 1,1-dioxide are stirred at room temperature for 3 hours under nitrogen with 0.71 g (4.6 mmol) of p-chlorophenylisocyanate and 0.47 g (4.6 mmol) of triethylamine in 10 ml of absolute dimethylsulfoxide. Thereafter, the mixture is poured into 40 ml of 2-N hydrochloric acid and 25 g of ice and stirred for 20 minutes. The separated precipitate is filtered off under suction and washed neutral with water. The precipitate is dissolved in 200 ml of methylene chloride, the turbid solution is dried over sodium sulfate, stirred with 0.3 g of active carbon and filtered. The filtrate is extracted with five 100 ml portions of saturated sodium carbonate solution, each of the aqueous phases being re-extracted with a small amount of methylene chloride. The combined aqueous phases are acidified to pH 1 with concentrated hydrochloric acid. The separated product is extracted with two 150 ml portions of methylene chloride. The combined organic phases are dried over sodium sulfate, whereupon the solvent is distilled off. For purification, the product is recrystallized from ca 50 ml of methanol. There is obtained 3-hydroxy-2-methyl-4-(4-chlorophenylcarbamoyl)-2H-thieno[3,2-e]-1,2-thiazine 1,1-dioxide of melting point 202°–204° C.

EXAMPLE 3

1 g (4.6 mmol) of 3,4-dihydro-2-methyl-3-oxo-2H-thieno[3,2-e]-1,2-thiazine 1,1-dioxide are stirred at room temperature for 3 hours under nitrogen with 0.82 g (4.6 mmol) of 2-methyl-4-nitrophenylisocyanate and 0.47 g (4.6 mmol) of triethylamine in 10 ml of absolute dimethyl sulfoxide. Thereafter, the mixture is poured into 40 ml of 2-N hydrochloric acid and 25 g of ice and stirred for 20 minutes. The separated precipitate is filtered off under suction and washed neutral with water. The precipitate is dissolved in 200 ml of methylene chloride, the turbid solution is dried over sodium sulfate, stirred with 0.3 g of active carbon and filtered. The filtrate is extracted with five 100 ml portions of saturated sodium carbonate solution, each of the aqueous phases being re-extracted with a small amount of methylene chloride. The combined aqueous phases are acidified to pH 1 with concentrated hydrochloric acid. The separated product is extracted with two 150 ml portions of methylene chloride. The combined organic phases are dried over sodium sulfate, whereupon the solvent is distilled off. For purification, the product is recrystallized from ca 80 ml methanol. There is obtained 3-hydroxy-2-methyl-4-(2-methyl-4-nitrophenylcarbamoyl)-2H-thieno[3,2-e]-1,2-thiazine 1,1-dioxide of melting point 189°–191° C.

EXAMPLE 4

1 g (4.6 mmol) of 3,4-dihydro-2-methyl-3-oxo-2H-thieno[3,2-e]-1,2-thiazine 1,1-dioxide are stirred at room temperature for 3 hours under nitrogen with 0.61 g (4.6 mmol) of benzylisocyanate and 0.47 g (4.6 mmol) of triethylamine in 10 ml of absolute dimethylsulfoxide. Thereafter, the mixture is poured into 40 ml of 2-N hydrochloric acid and 25 g of ice and stirred for 20 minutes. The separated precipitate is filtered off under suction and washed neutral with water. The precipitate is dissolved in 200 ml of methylene chloride, the turbid solution is dried over sodium sulfate, stirred with 0.3 g of active carbon and filtered. The filtrate is extracted with five 100 ml portions of saturated sodium carbonate solution, each of the aqueous phases being re-extracted with a small amount of methylene chloride. The combined aqueous phases are acidified to pH 1 with concentrated hydrochloric acid. The separated product is extracted with two 150 ml of methylene chloride. The combined organic phases are dried over sodium sulfate, whereupon the solvent is distilled off. For purification, the product is recrystallized from ca 40 ml of methanol. There is obtained 3-hydroxy-2-methyl-4-benzylcarbamoyl-2H-thieno[3,2-e]-1,2-thiazine 1,1-dioxide of melting point 176°–177° C.

EXAMPLE 5

1 g (4.6 mmol) of 3,4-dihydro-2-methyl-3-oxo-2H-thieno[3,2-e]-1,2-thiazine 1,1-dioxide are sitrred at room temperature for 3 hours under nitrogen with 0.71 g (4.6 mmol) of o-chlorophenylisocyanate and 0.47 g (4.6 mmol) of triethylamine in 10 ml of absolute dimethylsulfoxide. Thereafter, the mixture is poured into 40 ml of 2-N hydrochloric acid and 25 g of ice and stirred for 20 minutes. The separated precipitate is filtered off under suction and washed neutral with water. The precipitate is dissolved in 200 ml of methylene chloride, the turbid solution is dried over sodium sulfate, stirred with 0.3 g of active carbon and filtered. The filtrate is extracted with five 100 ml portions of saturated sodium carbonate solution, each of the aqueous phases being re-extracted with a small amount of methylene chloride. The combined aqueous phases are acidified to pH 1 with concentrated hydrochloric acid. The separated product is extracted with two 150 ml portions of methylene chloride. The combined organic phases are dried over sodium sulfate, whereupon the solvent is distilled off. For purification, the product is recrystallized from ca 50 ml of methanol. There is obtained 3-hydroxy-2-methyl-4-(2-chlorophenylcarbamoyl)-2H-thieno[3,2-e]-1,2-thiazine 1,1-dioxide of melting point 168°–170° C.

EXAMPLE 6

4 g (18.4 mmol) of 3,4-dihydro-2-methyl-3-oxo-2H-thieno[3,4-e]-1,2-thiazine 1,1-dioxide are stirred at room temperature under nitrogen for 24 hours with 3.6 g (18.4 mmol) of p-bromophenylisocyanate and 1.86 g (18.4 mmol) of triethylamine in 40 ml of absolute dimethylsulfoxide. Thereafter, the mixture is poured into 150 ml of 2-N hydrochloric acid and 100 g of ice and stirred for 20 minutes. The separated precipitate is filtered off under suction and washed neutral with water. The precipitate is taken up in 500 ml of methylene chloride, the turbid solution is dried over sodium sulfate, stirred with 1 g of active carbon and filtered. The filtrate is extracted with four 250 ml portions of semi-saturated sodium carbonate solution, each of the aqueous phases being re-extracted with a small amount of methylene chloride. The combined aqueous phases are acidified to pH 1 with concentrated hydrochloric acid. The separated product is extracted with three 300 ml portions of methylene chloride. The combined organic phases are dried over sodium sulfate and evaporated. The residual oil is covered with 5 ml of ethanol, the product separating out after standing for several days. The crystals are filtered off under suction, digested with a small amount of ethanol and dried. There is obtained 3-hydroxy-2-methyl-4-(4-bromophenylcarbamoyl)-2H-thieno[3,4-e]-1,2-thiazine 1,1-dioxide of melting point 138°–140° C.

The starting material is prepared as follows:

30 g (0.128 mol) of 4-N-methylsulfamoylthiophene-3-carboxylic acid methyl ester and 29 g (0.767 mol) of sodium borohydride are suspended in 700 ml of absolute ether and the suspension is heated to boiling. 73.5 g (2.30 mol) of absolute methanol, diluted with 300 ml of absolute ether, are added dropwise to the boiling suspension over a period of 30 minutes and then the mixture is boiled under reflux for 1 hour. After cooling, the mixture is cautiously hydrolyzed with 200 ml of half-concentrated hydrochloric acid. The separated precipitate is filtered off under suction. After separating the phases of the filtrate, the aqueous phase is extracted with three 300 ml portions of ether. The filter residue is digested with three 300 ml portions of ether. The combined organic phases are dried over sodium sulfate and evaporated to give an oil which crystallizes out upon cooling. There is obtained 3-hydroxymethyl-N-methyl-4-thiophenesulfonamide of melting point 118°–119° C.

23.8 g (0.115 mol) of 3-hydroxymethyl-N-methyl-4-thiophenesulfonamide are treated within 10 minutes with 120 ml of thionyl chloride and the mixture is boiled under reflux for 20 minutes. Thereafter, the mixture is evaporated to dryness in a water-jet vacuum. The residue is taken up in 500 ml of methylene chloride and stirred with saturated sodium bicarbonate solution until the aqueous phase has an alkaline reaction. The phases are separated and the aqueous phase is extracted with two 100 ml portions of methylene chloride. The combined organic phases are dried over sodium sulfate and evaporated. The residual oil crystallizes out upon cooling. There is obtained 3-chloromethyl-N-methyl-4-thiophenesulfonamide of melting point 75°–76° C.

26.5 g (0.109 mol) of 3-chloromethyl-N-methyl-4-thiophenesulfonamide and 21.3 g (0.328 mol) of potassium cyanide are warmed to 80° C. for 20 minutes in 130 ml of triethyleneglycol. Thereafter, the mixture is poured into 200 ml of 2-N hydrochloric acid and 200 g of ice and extracted with three 250 ml portions of methylene chloride. The combined organic phases are dried over sodium sulfate, stirred with 3 g of active carbon, filtered and evaporated. There is obtained 3-cyanomethyl-N-methyl-4-thiophenesulfonamide in the form of a non-crystallizing oil which is used in the next step without further purification.

22.9 g (0.098 mol) of 3-cyanomethyl-N-methyl-4-thiophenesulfonamide are boiled under reflux for 2 hours in a solution of 8.6 g (0.216 mol) of sodium hydroxide in 230 ml of water. After cooling, the mixture is acidified to pH 3 with ca 20 ml of concentrated hydrochloric acid and neutralized to pH 8 with sodium bicarbonate. The mixture is extracted with two 200 ml portions of methylene chloride. The organic phase is discarded. The aqueous phase is acidified to pH 1 with concentrated hydrochloric acid and extracted with methylene chloride for 24 hours. The organic phase is dried over sodium sulfate, stirred with active carbon, filtered and evaporated, whereby the product crystallizes out. There is obtained 3-(4-methylsulfamoyl)-thiopheneacetic acid of melting point 119°–120° C.

18.5 g (0.079 mol) of 3-(4-methylsulfamoyl)-thiopheneacetic acid are covered with 185 ml of thionyl chloride and boiled under reflux for 15 minutes. Thereafter, the mixture is evaporated to dryness in a water-jet vacuum. The residue is taken up in 250 ml of methylene chloride and stirred with saturated sodium bicarbonate solution until the aqueous phase has an alkaline reaction. The phases are separated. The aqueous phase is extracted with 100 ml of methylene chloride. The combined organic phases are dried over sodium sulfate and evaporated, whereby the product crystallizes out. For purification, the product is digested with a small amount of ice-cold methanol. There is obtained 3,4-dihydro-2-methyl-3-oxo-2H-thieno[3,4-e]-1,2-thiazine 1,1-dioxide of melting point 148°–149° C.

EXAMPLE 7

1 g (4.6 mmol) of 3,4-dihydro-2-methyl-3-oxo-2H-thieno[3,4]-1,2-thiazine 1,1-dioxide are stirred at room temperature for 3 hours under nitrogen with 0.71 g (4.6 mmol) of o-chlorophenylisocyanate and 0.47 g (4.6 mmol) of triethylamine in 10 ml of absolute dimethylsulfoxide. Thereafter, the mixture is poured into 40 ml of 2-N hydrochloric acid and 25 g of ice and stirred for 20 minutes. The separated precipitate is filtered off under suction and washed neutral with water. The precipitate is dissolved in 200 ml of methylene chloride, the turbid solution is dried over sodium sulfate, stirred with 0.3 g of active carbon and filtered. The filtrate is extracted with five 100 ml portions of saturated sodium carbonate solution, each of the aqueous phases being re-extracted with a small amount of methylene chloride. The combined aqueous phases are acidified to pH 1 with concentrated hydrochloric acid. The separated product is extracted with two 150 ml portions of methylene chloride. The combined organic phases are dried over sodium sulfate. The solvent is distilled off, whereby the product crystallizes out. For purification, the product is recrystallized from ca 30 ml of methanol. There is obtained 3-hydroxy-2-methyl-4-(2-chlorophenylcarbamoyl)-2H-thieno[3,4-e]-1,2-thiazine 1,1-dioxide of melting point 152°–155° C.

EXAMPLE 8

1 g (4.6 mmol) of 3,4-dihydro-2-methyl-3-oxo-2H-thieno[3,4-e]-1,2-thiazine 1,1-dioxide are stirred at room temperature under nitrogen for 3 hours with 0.82 g (4.6 mmol) of 2-methyl-4-nitrophenylisocyanate and 0.47 g (4.6 mmol) of triethylamine in 10 ml of absolute dimethylsulfoxide. Thereafter, the mixture is poured into 40 ml of 2-N hydrochloric acid and 25 g of ice and stirred for 20 minutes. The separated precipitate is filtered off under suction and washed neutral with water. The precipitate is dissolved in 200 ml of methylene chloride, the turbid solution is dried over sodium sulfate, stirred with 0.3 g of active carbon and filtered. The filtrate is extracted with five 100 ml portions of saturated sodium carbonate solution, each of the aqueous phases being re-extracted with a small amount of methylene chloride. The combined aqueous phases are acidified to pH 1 with concentrated hydrochloric acid. The separated product is extracted with two 150 ml portions of methylene chloride. The combined organic phases are dried over sodium sulfate. The solvent is distilled off, whereby the product crystallizes out. For purification, the product is recrystallized from ca 50 ml of methanol. There is obtained 3-hydroxy-2-methyl-4-(2-methyl-4-nitrophenylcarbamoyl)-2H-thieno[3,4-e]-1,2-thiazine 1,1-dioxide of melting point 186°–188° C.

EXAMPLE 9

1 g (4.6 mmol) of 3,4-dihydro-2-methyl-3-oxo-2H-thieno[3,4-e]-1,2-thiazine 1,1-dioxide are stirred at room temperature under nitrogen for 3 hours with 0.71 g (4.6 mmol) of p-chlorophenylisocyanate and 0.47 g (4.6 mmol) of triethylamine in 10 ml of absolute dimethylsulfoxide. Thereafter, the mixture is poured into 40 ml of 2-N hydrochloric acid and 25 g of ice and stirred for 20 minutes. The separated precipitate is filtered off under suction and washed neutral with water. The precipitate is dissolved in 200 ml of methylene chloride, the turbid solution is dried over sodium sulfate, stirred with 0.3 g of active carbon and filtered. The filtrate is extracted with five 100 ml portions of saturated sodium carbonate solution, each of the aqueous phases being re-extracted with a small amount of methylene chloride. The combined aqueous phases are acidified to pH 1 with concentrated hydrochloric acid. The precipitated product is extracted with two 150 ml portions of methylene chloride. The combined organic phases are dried over sodium sulfate. The solvent is distilled off, whereby the product crystallizes out. For purification, the product is recrystallized from ca 30 ml of methanol. There is obtained 3-hydroxy-2-methyl-4-(4-chlorophenylcarbamoyl)-2H-thieno[3,4-e]-1,2-thiazine 1,1-dioxide of melting point 154°–156° C.

The following Examples illustrate pharmaceutical preparations containing the thienothiazine derivatives provided by the present invention:

EXAMPLE A

Suppositories containing the following ingredients are produced in the usual manner:

| | |
|---|---|
| 3-Hydroxy-2-methyl-4-(4-bromophenylcarbamoyl)-2H-thieno[3,2-e]-1,2-thiazine 1,1-dioxide | 0.025 g. |
| Hydrogenated coconut oil | 1.230 g. |
| Carnauba wax | 0.045 g. |

EXAMPLE B

Tablets containing the following ingredients are produced in the usual manner:

| | Per Tablet |
|---|---|
| 3-Hydroxy-2-methyl-4-(4-bromophenylcarbamoyl)-2H-thieno[3,2-e]-1,2-thiazine 1,1-dioxide | 25.00 mg. |
| Lactose | 64.50 mg. |
| Maize starch | 10.00 mg. |
| Magnesium stearate | 0.50 mg. |

EXAMPLE C

Capsules containing the following ingredients are produced in the usual manner:

| | Per Capsule |
|---|---|
| 3-Hydroxy-2-methyl-4-(4-bromophenylcarbamoyl)-2H-thieno[3,2-e]-1,2-thiazene 1,1-dioxide | 50 mg. |
| Lactose | 125 mg. |
| Maize starch | 30 mg. |
| Talc | 5 mg. |
| Total Weight | 210 mg. |

We claim:

1. A compound of the formula

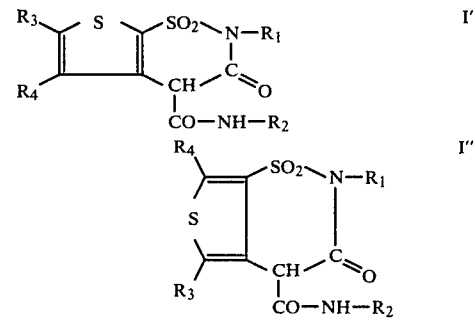

wherein $R_1$ is lower alkyl, $R_2$ is an unsubstituted aromatic heterocyclic radical selected from the group consisting of 2-thiazolyl, 4-methyl-2-thiazolyl, 4,5-dimethyl-2-thiazolyl, 5-methyl-1,3,4-thiadiazolyl, 2-pyrazinyl, 2-pyrimidinyl, 1,2,4-triazin-2-yl, 2-pyridyl, 3-pyridyl, 4-pyridyl, 3-methyl-2-pyridyl, 4-methyl-2-pyridyl, 5-methyl-2-pyridyl, 6-methyl-2-pyridyl, 4,6,-dimethyl-2-pyridyl, 5-isoxazolyl, 5-methyl-3-isoxazolyl, 3,4-dimethyl-5-isoxazolyl, 2,6-dimethyl-4-pyrimidinyl or 1,2,3,4-tetrazol-5-yl; a phenyl radical, or a phenyl or benzyl group optionally substituted by halogen, hydroxy, lower alkyl, trifluoromethyl or lower alkoxy, and $R_3$ and $R_4$, individually, are hydrogen or lower alkyl, its tautomer, a salt thereof with a pharmaceutically acceptable base and, when $R_2$ is the residue of a basic heterocycle, a salt thereof with a pharmaceutically accetpable strong acid.

2. A compound in accordance with claim 1, wherein R₃ and R₄ are hydrogen, R₁ is methyl and R₂ is phenyl or halogenated phenyl.

3. A compound in accordance with claim 1, 3-hydroxy-2-methyl-4-(4-bromophenylcarbamoyl)-2H-thieno[3,2-e] -1,2-thiazine 1,1-dioxide.

4. A compound in accordance with claim 1, 3-hydroxy-2-methyl-4-(4-chlorophenylcarbamoyl)-2H-thieno[3,2-e] -1,2-thiazine 1,1-dioxide.

5. A compound in accordance with claim 1, 3-hydroxy-2-methyl-4-(2-methyl-4-nitrophenylcarbamoyl)-2H-thieno[3,2-e]-1,2-thiazine 1,1-dioxide.

6. A compound in accordance with claim 1, 3-hydroxy-2-methyl-4-benzylcarbamoyl-2H-thieno[3,2-e] -1,2-thiazine 1,1-dioxide.

7. A compound in accordance with claim 1, 3-hydroxy-2-methyl-4-(2-chlorophenylcarbamoyl)-2H-thieno[3,2-e] -1,2-thiazine 1,1-dioxide.

8. A compound in accordance with claim 1, 3-hydroxy-2-methyl-4-(4-bromophenylcarbamoyl)-2H-thieno[3,4-e] -1,2-thiazine1,1-dioxide.

9. A compound in accordance with claim 1, 3-hydroxy-2-methyl-4-(2-chlorophenylcarbamoyl)-2H-thieno[3,4-e] -1,2-thiazine 1,1-dioxide.

10. A compound in accordance with claim 1, 3-hydroxy-2-methyl-4-(2-methyl-4-nitrophenylcarbamoyl)-2H-thieno[3,4-e] -1,2-thiazine 1,1-dioxide.

11. A compound in accordance with claim 1, 3-hydroxy-2-methyl-4-(4-chlorophenylcarbamoyl)-2H-thieno[3,4-e] -1,2-thiazine 1,1-dioxide.

12. A pharmaceutical preparation comprising a compound of the formula

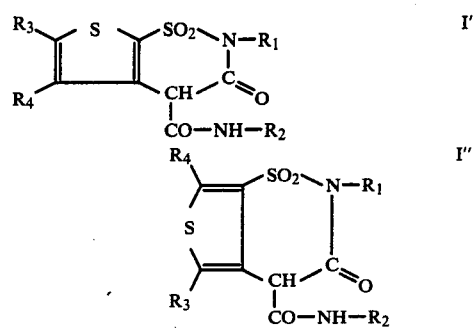

wherein $R_1$ is lower alkyl, $R_2$ is an unsubstituted aromatic heterocyclic radical selected from the group consisting of 2-thiazolyl, 4-methyl-2-thiazolyl, 4,5-dimethyl-2-thiazolyl, 5-methyl-1,3,4-thiadiazolyl, 2-pyrazinyl, 2-pyrimidinyl, 1,2,4-triazin-2-yl, 2-pyridyl, 3-pyridyl, 4-pyridyl, 3-methyl-2-pyridyl, 4-methyl-2-pyridyl, 5-methyl-2-pyridyl, 6-methyl-2-pyridyl, 4,6,-dimethyl-2-pyridyl, 5-isoxazolyl, 5-methyl-3-isoxazolyl, 3,4-dimethyl-5-isoxazolyl, 2,6-dimethyl-4-pyrimidinyl or 1,2,3,4-tetrazol-5-yl; a phenyl radical, or a phenyl or benzyl group optionally substituted by halogen, hydroxy, lower alkyl, trifluoromethyl or lower alkoxy, and $R_3$ and $R_4$, individually, are hydrogen or lower alkyl, its tautomer, a salt thereof with a pharmaceutically acceptable base and, when $R_2$ is the residue of a basic heterocycle, a salt thereof with a pharmaceutically accetpable strong acid, in association with a compatible pharmaceutical carrier material.

* * * * *